United States Patent [19]

Gruetzmacher

[11] Patent Number: 4,567,048
[45] Date of Patent: Jan. 28, 1986

[54] INDIGOID DYES

[75] Inventor: Gordon D. Gruetzmacher, Gales Ferry, Conn.

[73] Assignee: Pfizer Inc., New York, N.Y.

[21] Appl. No.: 605,316

[22] Filed: Apr. 30, 1984

Related U.S. Application Data

[63] Continuation-in-part of Ser. No. 453,635, Dec. 27, 1982, abandoned.

[51] Int. Cl.$^4$ ............... A23L 1/275; C07D 209/36
[52] U.S. Cl. ............................. 426/250; 426/540; 548/460
[58] Field of Search ............... 548/460; 426/540, 250

[56] References Cited

U.S. PATENT DOCUMENTS 2,043,081  6/1936  Wahl .................................. 542/442
2,777,845  1/1957  Oken et al. ......................... 548/460

Primary Examiner—Donald G. Daus
Assistant Examiner—Mary E. Ceperley
Attorney, Agent, or Firm—Charles J. Knuth; Peter C. Richardson

[57] ABSTRACT

A series of novel water-soluble sulfonated indoxyl derivatives have been prepared, including their base salts with pharmacologically acceptable cations. These particular compounds are useful as food dyes or as cosmetic colorants. 2,2'-(1,4-phenylenedimethylidyne)-bis(2,3-dihydro-3-oxo-1H-indole-5-sulfonic acid) represents a typical and preferred member compound. Methods for preparing these compounds are provided.

10 Claims, No Drawings

INDIGOID DYES

CROSS REFERENCE TO RELATED APPLICATION

This application is a continuation-in-part of co-pending application Ser. No. 453,635, filed Dec. 27, 1982, now abandoned.

BACKGROUND OF THE INVENTION

This invention relates to new and useful indigoid dyes. More particularly, it is concerned with a novel series of water-soluble sulfonated indoxyl derivatives, which are of especial value in the field of food chemistry, in view of their unique physiochemical properties as food dyes, and as cosmetic colorants.

SUMMARY OF THE INVENTION

Thus, according to the present invention, there are now provided for the first time compounds of the formula:

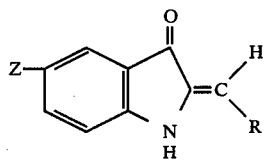

and the base salts thereof with pharmacologically acceptable cations, wherein Z is sulfonylhydroxy and R is a moiety of the formula:

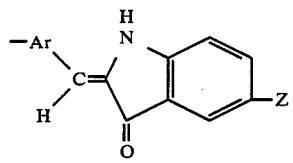

wherein Z is as previously defined and Ar represents a divalent aromatic radical chosen from the group consisting of 1,4-phenylene, 1,3-phenylene, 2,5-dimethoxy-1,4-phenylene, 4,6-dimethoxy-1,3-phenylene, 4-dimethylamino-1,3-phenylene, 1,4-naphthylene and 2,6-naphthylene. These compounds are all water-soluble and give red to yellow solutions with good tinctorial properties.

Typical member compounds of the present invention include such bis-indigoid dyes as 2,2'-(1,4-phenylenedimethylidyne)-bis(2,3-dihydro-3-oxo-1H-indole-5-sulfonic acid), 2,2'-(1,3-phenylenedimethylidyne)-bis(2,3-dihydro-3-oxo-1H-indole-5-sulfonic acid), 2,2'-(2,5-dimethoxy-1,4-phenylenedimethylidyne)-bis(2,3-dihydro-3-oxo-1H-indole-5-sulfonic acid), 2,2'-(4,6-dimethylamino-1,3-phenylenedimethylidyne)-bis(2,3-dihydro-3-oxo-1H-indole-5-sulfonic acid), 2,2'-(4-dimethylamino-1,3-phenylene)-bis(2,3-dihydro-3-oxo-1H-indole-5-sulfonic acid), 2,2'-(1,4-naphthylenedimethylidyne)-bis(2,3-dihydro-3-oxo-1H-indole-5-sulfonic acid) and 2,2'-(2,6-naphthylenedimethylidyne)-bis(2,3-dihydro-3-oxo-1H-indole-5-sulfonic acid), respectively. The most preferred member compound of the invention is 2,2'-(1,4-phenylenedimethylidyne)-bis(2,3-dihydro-3-oxo-1H-indole-5-sulfonic acid).

The invention also includes within its scope a food or cosmetic composition suitable for human use comprising a biocompatible carrier and an effective amount of a dye or coloring compound of the structural formula previously indicated. The invention additionally provides a method for coloring foods or cosmetics by incorporating therein an effective amount of a dye or coloring compound of the same aforesaid structural formula.

DETAILED DESCRIPTION OF THE INVENTION

In accordance with the principal process employed for preparing the novel compounds of this invention, an appropriate aromatic dialdehyde is (1) condensed with indoxyl acetate in either an acid or base-catalyzed manner to form the corresponding water-soluble indigoid compound, which is then (2) sulfonated with concentrated sulfuric acid to yield the desired final product. The preferred condensation reaction in the first step is the acid-catalyzed reaction since it is under these conditions that the amount of indigo by-product formation is generally reduced. In this way, terephthaldehyde is condensed with indoxyl acetate (in an acid-catalized manner) to form 2,2'-(1,4-phenylenedimethylidyne)-bis(1,2-dihydro-3H-indol-3-one) which, in turn, is then converted to 2,2'-(1,4-phenylenedimethylidyne)-bis(2,3-dihydro-3-oxo-1H-indole-5-sulfonic acid).

The starting materials required for preparing the novel compounds of this invention, viz., the dialdehydes used in the synthesis of the aforesaid indigoids, are all known compounds that are either commercially available or else easily prepared from known literature procedures (see Preparations A–H). Indoxyl acetate is a commercially available material.

The chemical bases which are used as reagents in this invention to prepare the aforementioned pharmacologically acceptable base salts are those which form non-toxic salts with the herein described acidic sulfonated indoxyl derivatives, such as 2,2'-(1,4-phenylenedimethylidyne)-bis(2,3-dihydro-3-oxo-1H-indole-5-sulfonic acid), for example. These particular non-toxic base salts are of such a nature that their cations are essentially non-toxic in character over the wide range of dosage administered. Examples of such cations include those of sodium, potassium, calcium and magnesium, etc. These salts can easily be prepared by simply treating the aforementioned sulfonated indoxyl derivatives with an aqueous solution of the desired pharmacologically acceptable base, such as the hydroxide, carbonate or bicarbonate of one of the aforementioned cations, and then evaporating the resulting solution to dryness while preferably being placed under reduced pressure. Alternatively, they may also be prepared by mixing lower alkanolic solutions of the said acidic compounds and the desired alkali metal alkoxide together and then evaporating the resulting solution to dryness in the same manner as before. In either case, stoichiometric quantities of reagents should be employed in order to ensure completeness of reaction and maximum yields of the desired final product.

As previously indicated, the water-soluble sulfonated indoxyl derivatives of the present invention are particularly valuable as food dyes and as cosmetic colorants and hence, are of use in the preparation and compounding of various food and cosmetic compositions. These dyes all give clear sparkling aqueous solutions. Moreover, these dyes are poorly absorbed in the gastrointestinal tract and hence, are particularly useful for human consumption. For instance, 2,2'-(1,4-phenylenedimethylidyne)-bis(2,3-dihydro-3-oxo-1H-indole-5-sulfonic acid), a typical and preferred agent of the present invention, gives red aqueous solutions similar to Amaranth (formerly FD&C Red No. 2), while metabolism studies have shown that this compound is virtually non-absorbed (1% detectable limit) from the gastrointestinal tract of rats and mice and is metabolized, presumably by the microflora present in the gut, to 5-sulfoisatin and 5-sulfoanthranilic acid so that no unchanged compound remains in the feces (this fecal metabolism pattern is similar to that of FD&C Blue No. 2, which is indigo carmine). The other compounds of this invention also cause similar results, with the colors ranging, for the most part, in the red and yellow area.

As will be understood by those skilled in the art, the food dyes and cosmetic colorants of the present invention are suitable for human use in the same type formulations formerly associated with Amaranth (formerly FD&C Red No. 2), as well as with FD&C Red No. 40 and FD&C Blue No. 2 (indigo carmine). In all these formulations, the biocompatible carrier (with water being a prime example) is always selected and applied in accordance with the known standard practice in the field.

In the Preparations and Examples which follow, a list of all the indigoids synthesized is provided wherein the wave length of maximum absorption ($\lambda$ max) and % absorbance of a 0.1% solution (which is a measure of tinctorial strength) is reported for each compound.

PREPARATION A

A solution consisting of 10.0 g (0.057 mole) of indoxyl acetate and 3.83 g (0.0285 mole) of terephthalaldehyde dissoved in 370 ml. of methanol was placed under a dry nitrogen atmosphere in a 2-liter round-bottomed reaction flask equipped with gas-inlet tube and reflux condenser. At this point, 500 ml of water was added to the mixture and a solid precipitate soon formed. On heating the mixture to reflux, complete solution was again achieved. The resulting aqueous solution was then treated with 10 ml. of concentrated hydrochloric acid (added through the top of the reflux condenser) and the resulting mixture turned red and soon afforded a solid precipitate (solids began to appear ca. 2-3 minutes after the addition). The reaction mixture was then refluxed for a period of 50 minutes and cooled to room temperature ($\sim 25°$ C.). After cooling in an ice bath, the resulting red solids were recovered from the spent reaction mixture by means of suction filtration and washed successively with 250 ml portions of water, methanol and acetone, respectively. The resultant red product was then dried overnight ($\sim 16$ hours) in a vacuum oven to afford 8.97 g (86%) of pure 2,2'-(1,4-phenylenedimethylidyne)-bis(1,2-3H-indol-3-one), m.p.>250° C.

Anal. Calcd. for $C_{24}H_{16}N_2O_4.0.5H_2O$: C, 77.19; H, 4.59; N, 7.50. Found: C, 76.96; H, 4.52; N, 7.49.

PREPARATION B

The procedure described in Preparation A was repeated except that 2,5-dimethoxyterephthaldehyde was the reagent employed instead of terephthalaldehyde, using the same molar proportions as before. In this particular case, the corresponding final product obtained was 2,2'-(2,5-dimethoxy-1,4-phenylenedimethylidyne)-bis-(1,2-dihydro-3H-indole-3-one), m.p. >250° C.;

$\lambda_{max}^{EtOH}$ at 566 nm($A_{1\ cm}^{0.1\%} = 66.2\%$).

Anal. Calcd. for $C_{26}H_{20}N_2O_6.3.5H_2O$: C, 64.06; H, 5.58; N, 5.75. Found: C, 64.19; H, 5.58; N, 5.75.

PREPARATION C

The procedure described in Preparation A was repeated except that isophthalaldehyde was the reagent employed instead of terephthalaldehyde, using the same molar proportions as before. In this particular case, the corresponding final product obtained was 2,2'-(1,3-phenylenedimethylidyne)-bis(1,2-dihydro-3H-indol-3-one), m.p.>250° C.; $\lambda_{max}^{EtOH}$ at 482 nm($A_{1\ cm}^{0.1\%} = 62.2\%$).

Anal. Calcd. for $C_{24}H_{16}N_2O_4$:C, 79.11; H, 4.43; N, 7.69. Found: C, 78.97; H, 4.63; N, 7.59.

PREPARATION D

The procedure described in Preparation A was repeated except that 2,6-naphthaldehyde was the reagent employed instead of terephthaldehyde, using the same molar proportions as before. In this particular case, the corresponding final product obtained was 2,2'-(2,6-naphthylenedimethylidyne)-bis(1,2-dihydro-3H-indol-3-one), m.p. >250° C.; $\lambda_{max}^{EtOH}$ at 495 nm ($A_{1\ cm}^{0.1\%} = 13.2\%$).

Anal. Calcd. for $C_{28}H_{18}N_2O_4.0.5H_2O$: C, 79.42; H, 4.62; N, 6.61. Found: C, 79.84; H, 4.40; N, 6.34.

PREPARATION E

The procedure described in Preparation A was repeated except that 1,4-naphthaldehyde was the reagent employed instead of terephthaldehyde, using the same molar proportions as before. In this particular case, the corresponding final product obtained was 2,2'-(1,4-naphthylenedimethylidyne)-bis(1,2-dihydro-3H-indol-3-one), m.p. >250° C.; $\lambda$EtOH at 526 nm ($A_{1\ cm}^{0.1\%} = 51.4\%$).

Anal. Calcd. for $C_{28}H_{18}N_2O_4S$: C, 81.14; H, 4.38; N, 6.76. Found: C, 80.65; H, 4.62; N, 6.75.

PREPARATION F

To a solution consisting of 42 g of sodium hydroxide dissolved in 700 ml. of water contained in a three-necked round-bottomed reaction flask, there were added 20.0 g. (0.114 mole) of indoxyl acetate. The reaction flask was equipped with reflux condenser, nitrogen-inlet tube and glass dropping funnel. Stirring was commenced and the entire system was placed under a nitrogen atmosphere prior to heating in an oil bath maintained at a bath temperature of ca. 124° C. The mixture was soon brought to reflux (in approximately 25 minutes) and maintained at the latter point for a period of one hour, during which time the bath temperature rose to ca. 135° C. At this point, a solution consisting of 17.0 g. (0.114 mole) of p-dimethylaminobenzaldehyde in 160 ml. of ethanol was added from the dropping funnel (slowly) during the course of a ten-minute period and the resulting reaction mixture was then refluxed for a period of two hours. After cooling to room temperature ($\sim 25°$ C.) with the aid of an ice bath, the solid product was recovered by means of suction filtration, washed on the filter funnel with a little water and dried in a vacuum oven at 50° C. for a period of approximately 16 hours (i.e., overnight). The total yield of crude material amounted to 23.74 g. This material was subsequently washed with four-900 ml. portions of n-hexane and air dried to constant weight (yield, 20.72 g.), followed by dissolution in 3500 ml. of hot ethyl acetate. After filtering the latter solution, the filtrate was allowed to stand overnight (~16 hours) at room temperature and a fine crystalline crop (m.p. 235°–237° C.) was subsequently collected (yield, 12.64 g.). The resulting filtrate was then vacuum stripped to a volume of 900 ml., at which point sufficient fresh ethyl acetate was added to the mixture to bring the total volume to 1100 ml. and the resultant organic solution was again heated and filtered while hot. This second filtrate then allowed to cool to room temperature and another crystalline crop (m.p. 233°–236° C.) was collected (yield, 4.21 g.). The final filtrate was then boiled down to 500 ml. and allowed to cool overnight. In this way, a third crystalline crop (m.p. 231°–235° C. was also obtained (yield, 1.13 g.). The total yield of pure 2-[(4-dimethylaminophenyl)methylene]-1,2-dihydro-3H-indol-3-one amounted to 17.98 g. (59.7%). The combined recrystallized sample (from hot ethyl acetate) melted at 235°–238° C. [lit. m.p. 236°–238° C., according to Can. J. Chem., 38, 131 (1960)]; $\lambda_{max}^{EtOH}$ at 511 nm ($A_{1\,cm}^{0.1\%}$=112%).

PREPARATION G

The procedure described in Preparation F was repeated except that 4-dimethylaminoisophthalaldehyde [Angew. Chem., 77, 955 (1965)] was the reagent employed instead of p-dimethylaminobenzaldehyde, using a molar proportion of one part aldehyde to two parts of indoxyl acetate. In this particular case, the corresponding final product obtained was 2,2'-(4-dimethylamino-1,3-phenylenedimethylidyne)-bis(1,2-dihydro-3H-indol-3-one), m.p. >250° C.

Anal. Calcd. for $C_{26}H_{21}N_3O_2.0.5H_2O$: C, 74.98; H, 5.32; N, 10.09. Found: C, 75.04; H, 5.38; N, 10.08.

PREPARATION H

The procedure described in Preparation A was repeated except that 4,6-dimethoxyisophthaldehyde was the reagent employed instead of terephthaldehyde, using the same molar proportions as before. In this particular case, the corresponding final product obtained was 2,2'-(4,6-dimethoxy-1,3-phenylenedimethylidyne)-bis(1,2-dihydro-3H-indol-3-one), m.p. >250° C.; $\lambda_{max}^{EtOH}$ at 484 nm ($A_{1\,cm}^{0.1\%}$=54.1%).

Anal. Calcd. for $C_{26}H_{20}N_2O_6$: C, 73.57; H, 4.75; N, 6.45. Found: C, 73.41; H, 5.09; N, 6.62.

EXAMPLE 1

In a 15 ml. round-bottomed reaction flask, there were placed 1.0 g. (0.00275 mole) of 2,2'-(1,4-phenylenedimethylidyne)-bis(1,2-dihydro-3H-indol-3-one) and 10 ml. of concentrated sulfuric acid while under a dry nitrogen atmosphere. The entire system was then placed in an oil-bath preheated to 80° C. and stirred and heated at that point for a period of 20 minutes. The spent reaction mixture was then poured into 10 g. of cracked ice contained in a beaker and the total volume was brought up to 30 ml. by adding fresh water used to rinse the original reaction flask. The resulting solids were then collected by means of suction filtration and subsequently taken up in 100 ml. of acetone and filtered. The recovered material was then taken up in 150 ml. of ethyl acetate and centrifuged and this procedure was repeated once, before drying the crude material overnight (~16 hours). The dried product was then taken up in 100 ml. of fresh ethyl acetate and filtered, followed by a final treatment with 100 ml. of acetone before drying in a vacuum oven overnight to ultimately afford 1.16 g. (81%) of pure 2,2'-(1,4-phenylenedimethylidyne)-bis(2,3-dihydro-3-oxo-1H-indole-5-sulfonic acid), m.p. >250° C.; $\lambda_{max}^{H2O}$ at 534 nm ($A_{1\,cm}^{0.1\%}$=41.5%).

Anal. Calcd. for $C_{24}H_{16}N_2O_8S_2.3H_2O$: C,49.82; H,3.83; N, 4.84. Found: C, 50.10; H, 4.07; N, 4.73.

EXAMPLE 2

The procedure described in Example 1 was repeated except that 2,2'-(2,5-dimethoxy-1,4-phenylenedimethylidyne)-bis(1,2-dihydro-3H-indol-3-one) was the starting material employed in place of 2,2'-(1,4-phenylenedimethylidyne)-bis(1,2-dihydro-3H-indol-3-one), using the same molar proportions as before. In this particular case, the corresponding final product obtained was 2,2'-(2,5-dimethoxy-1,4-phenylenedimethylidyne)-bis(2,3-dihydro-3-oxo-1H-indole-5-sulfonic acid), m.p. >250° C.; $\lambda_{max}^{H2O}$ at 548 nm ($A_{1\,cm}^{0.1\%}$=30.0%) Anal. Calcd. for $C_{26}H_{20}N_2O_{10}S_2.0.6H_2O$: C, 45.08; H, 4.66; N, 4.04. Found: C, 45.13; H, 4.04; N, 4.13.

EXAMPLE 3

The procedure described in Example 1 was repeated except that 2,2'-(1,3-phenylenedimethylidyne)-bis(1,2-dihydro-3H-indol-3-one) was the starting material employed in place of 2,2'-(1,4-phenylenedimethylidyne)-bis(1,2-dihydro-3H-indol-3-one), using the same molar proportions as before. In this particular case, the corresponding final product obtained was 2,2'-(1,3-phenylenedimethylidyne)-bis(2,3-dihydro-3-oxo-1H-indole-5-sulfonic acid), m.p. >250° C.; $\lambda_{max}^{H2O}$ at 487 nm ($A_{1\,cm}^{0.1\%}$=37.8%).

Anal. Calcd. for $C_{24}H_{16}N_2O_8S_2.0.2.5H_2O$: C, 50.61; H, 3.72; N, 4.92. Found: C, 50.66; H, 4.02; N, 4.82.

EXAMPLE 4

The procedure described in Example 1 was repeated except that 2,2'-(2,6-naphthylenedimethylidyne)-bis(1,2-dihydro-3H-indol-3-one) was the starting material employed in place of 2,2'-(1,4-phenylenedimethylidyne)-bis(1,2-dihydro-3H-indol-3-one), using the same molar proportions as before. In this particular case, the corresponding final product obtained was 2,2'-(2,6-naphthylenedimethylidyne)-bis(2,3-dihydro-3-oxo-1H-indole-5-sulfonic acid), m.p. >250° C.; $\lambda_{max}^{H2O}$ at 496 nm ($A_{1\,cm}^{0.1\%}$=25.6%).

Anal. Calcd. for $C_{28}H_{18}N_2O_8S_2.0.8H_2O$: C, 46.79; H, 4.77; N, 3.90. Found: C, 46.65; H, 3.94; N, 3.83.

EXAMPLE 5

The procedure described in Example 1 was repeated except that 2,2'-(1,4-naphthylenedimethylidyne)-bis(1,2-dihydro-3H-indol-3-one) was the starting material employed in place of 2,2'-(1,4-phenylenedimethylidyne)-bis(1,2-dihydro-3H-indol-3-one), using the same molar proportions as before. In this particular case, the corresponding final product obtained was 2,2'-(1,4-naphthylenedimethylidyne)-bis(2,3-dihydro-3-oxo-1H-indole-5-sulfonic acid), m.p. >250° C.; $\lambda_{max}^{H2O}$ at 534 nm ($A_{1\,cm}^{0.1\%}$=48.5%).

Anal. Calcd. for $C_{28}H_{18}N_2O_8S_2.0.2.5H_2O$: C, 54.28; H, 3.75; N, 4.52. Found: C, 54.29; H, 3.92; N, 4.68.

EXAMPLE 6

The procedure described in Example 1 was repeated except that 2,2'-(4-dimethylamino-1,3-phenylenedimethylidyne)-bis(1,2-dihydro-3H-indol-3-one) was the starting material employed in place of 2,2'-(1,4-phenylenedimethylidyne)-bis(1,2-dihydro-3H-indol-3-one), using the same molar proportions as before. In this particular case, the corresponding final product obtained was 2,2'-(4-dimethylamino-1,3-phenylenedimethylidyne)-bis(2,3-dihydro-3-oxo-1H-indole-5-sulfonic acid), m.p. >250° C.; $\lambda_{max}^{H2O}$ at 499 nm ($A_{1\ cm}^{0.1\%}$=32.9%).

Anal. Calcd. for $C_{30}H_{21}N_3O_8S_2O.8.5H_2O$: C, 43.34; H, 5.31; N, 5.83. Found: C, 43.24; H, 4.87; N, 5.78.

EXAMPLE 7

The procedure described in Example 1 was repeated except that 2,2'-(4,6-dimethoxy-1,3-phenylenedimethylidyne)-bis(1,2-dihydro-indol-3-one) was the starting material employed in place of 2,2'-(1,4-phenylenedimethylidyne)-bis(1,2-dihydro-3H-indol-3-one), using the same molar proportions as before. In this particular case, the corresponding final product obtained was 2,2'-(4,6-dimethoxy-1,3-phenylenedimethylidyne)-bis(2,3-dihydro-3-oxo-1H-indole-5-sulfonic acid), m.p. >250° C.; $\lambda_{max}^{H2O}$ at 507 nm ($A_{1\ cm}^{0.1\%}$=35.5%).

Anal. Calcd. for $C_{26}H_{20}N_2O_{15}S_2O.6H_2O$: C, 45.08; H, 4.66; N, 4.04. Found: C, 45.13; H, 4.04; N, 4.13.

I claim:

1. A compound selected from the group consisting of water-soluble sulfonated indoxyl derivatives of the formula:

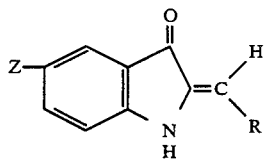

and the base salts thereof with pharmacologically acceptable cations, wherein Z is sulfonylhydroxy and R is a moiety of the formula:

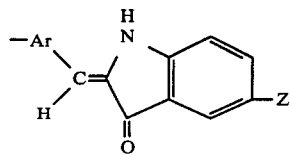

wherein Z is as previously defined and Ar represents a divalent aromatic radical chosen from the group consisting of 1,4-phenylene, 1,3-phenylene, 2,5-dimethoxy-1,4-phenylene, 4,6-dimethoxy-1,3-phenylene, 4-dimethylamino-1,3-phenylene, 1,4-naphthylene and 2,6-naphthylene.

2. A compound as claimed in claim 1 wherein Ar is 1,4-phenylene.

3. A compound as claimed in claim 1 wherein Ar is 1,3-phenylene.

4. A compound as claimed in claim 1 wherein Ar is 2,5-dimethoxy-1,4-phenylene,

5. A compound as claimed in claim 1 wherein Ar is 4,6-dimethoxy-1,3-phenylene.

6. A compound as claimed in claim 1 wherein Ar is 4-dimethylamino-1,3-phenylene.

7. A compound as claimed in claim 1 wherein Ar is 1,4-naphthylene.

8. A compound as claimed in claim 1 wherein Ar is 2,6-naphthylene.

9. 2,2'-(1,4-Phenylenedimethylidyne)-bis(2,3-dihydro-3-oxo-1H-indole-5-sulfonic acid).

10. A method for coloring foods which comprises incorporating therein an effective amount of a dye or coloring compound as claimed in claim 1.

* * * * *